(12) United States Patent
Lesage et al.

(10) Patent No.: US 8,336,383 B2
(45) Date of Patent: *Dec. 25, 2012

(54) METHOD AND APPARATUS FOR AUTOMATIC NON-DESTRUCTIVE TESTING OF TUBULAR AXLE SHAFTS WITH VARIABLE INTERNAL AND EXTERNAL RADIUS PROFILES

(75) Inventors: Frederic Lesage, Saint-Saulve (FR); Alexandre Noel, Englefontaine (FR); Renato Nogueira De Paula, Valenciennes (FR)

(73) Assignee: V & M France, Boulogne-Billancourt (FR)

( * ) Notice: Subject to any disclaimer, the term of this patent is extended or adjusted under 35 U.S.C. 154(b) by 407 days.

This patent is subject to a terminal disclaimer.

(21) Appl. No.: 12/665,477

(22) PCT Filed: Jun. 16, 2008

(86) PCT No.: PCT/FR2008/000836
§ 371 (c)(1),
(2), (4) Date: Dec. 18, 2009

(87) PCT Pub. No.: WO2009/010653
PCT Pub. Date: Jan. 22, 2009

(65) Prior Publication Data
US 2010/0170344 A1    Jul. 8, 2010

(30) Foreign Application Priority Data
Jun. 21, 2007   (FR) ..................... 07 04435

(51) Int. Cl.
*G01N 29/00* (2006.01)
*G01M 17/007* (2006.01)

(52) U.S. Cl. ..................... 73/632; 73/115.07

(58) Field of Classification Search ............ 73/632, 73/115.07, 116, 116.04, 146, 865.9
See application file for complete search history.

(56) References Cited

U.S. PATENT DOCUMENTS
4,800,748 A * 1/1989 Fischer et al. ............ 73/865.9
(Continued)

FOREIGN PATENT DOCUMENTS
BE    1014836    * 5/2004
(Continued)

OTHER PUBLICATIONS
U.S. Appl. No. 12/665,343, filed Dec. 18, 2009, Lesage, et al.
(Continued)

*Primary Examiner* — J M Saint Surin
(74) *Attorney, Agent, or Firm* — Oblon, Spivak, McClelland, Maier & Neustadt, L.L.P.

(57) ABSTRACT

An apparatus testing axle shafts includes i) a test bench to receive a tubular axle shaft including a wall exhibiting variable known external and internal radius profiles, ii) at least one ultrasonic probe to analyze at least one selected portion of the wall in a selected angular sector and thus acquire analysis data, iii) a controller to control the test bench to place each probe on the wall external or internal surface in at least one first site selected as a function of its profiles and a possible loading of the shaft such that it analyses the first and second selected wall portions respectively in at least one first and at least one second selected angular sector oriented in first and second opposing longitudinal or transverse directions, to thus acquire analysis data for various relative angular positions of the shaft in relation to the probe, and iv) a processor to create from these acquired analysis data maps representing the transverse or longitudinal orientations and positions of indications of echoes within the wall.

37 Claims, 4 Drawing Sheets

U.S. PATENT DOCUMENTS

Figure 1:
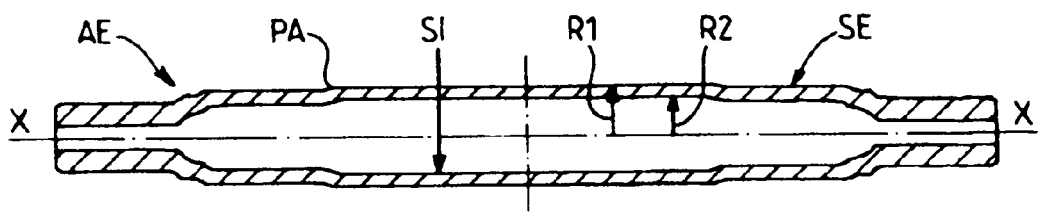

| | | | |
|---|---|---|---|
| 4,893,511 A * | 1/1990 | Voigt et al. | 73/622 |
| 4,898,026 A | 2/1990 | Damitz | |
| 4,939,985 A * | 7/1990 | Von Thun | 73/116.01 |
| 4,951,504 A * | 8/1990 | Klock et al. | 73/117.03 |
| 5,426,978 A | 6/1995 | Imai | |
| 6,886,407 B1 | 5/2005 | Fredenberg | |
| 6,945,114 B2 * | 9/2005 | Kenderian et al. | 73/643 |
| 2002/0194916 A1 | 12/2002 | Yamada et al. | |
| 2010/0180683 A1 * | 7/2010 | Lesage et al. | 73/618 |
| 2010/0191515 A1 * | 7/2010 | Walenta et al. | 703/6 |

FOREIGN PATENT DOCUMENTS

| | | |
|---|---|---|
| CN | 1393692 A | 1/2003 |
| CN | 1570620 A | 1/2005 |
| DE | 36 42 717 | 6/1988 |
| DE | 43 34 632 | 4/1994 |
| DE | 20 2004 015 456 | 11/2005 |
| JP | 57-20660 A | 2/1982 |
| JP | 2002-82099 | 3/2002 |
| JP | 2002 257798 | 9/2002 |
| RU | 2 084 889 C1 | 7/1997 |
| RU | 2 086 975 C1 | 8/1997 |
| RU | 2 313 784 C1 | 12/2007 |
| WO | 2006 099397 | 9/2006 |

OTHER PUBLICATIONS

A. Erhard, et al., "Ultrasonic Phased Array System for Railroad Axle Examination", NDT.net, vol. 8, No. 3, Mar. 2003, 6 pages.

* cited by examiner

METHOD AND APPARATUS FOR AUTOMATIC NON-DESTRUCTIVE TESTING OF TUBULAR AXLE SHAFTS WITH VARIABLE INTERNAL AND EXTERNAL RADIUS PROFILES

The invention relates to axle shafts which are used for example in the field of railways, and more specifically the testing (or the inspection) of such shafts using non-destructive technique(s).

As the expert is aware, some axle shafts, and in particular those which must support substantial loads, must undergo non-destructive tests at different stages of production and maintenance in order to meet international standards. Known non-destructive testing methods are quite well adapted to solid axle shafts. They are typically based on an acoustic analysis, using ultrasonic probes, and possibly on an additional analysis such as for example a surface analysis or radiographic analysis. Standards to be fulfilled by solid axle shafts include in particular NF EN 13261-2004 for Europe, ISO 5948-1994 and ISO 6933-1986 for the world, M 101/90-A for the USA (Association of American Railroads (AAR)), NBR 7947-1989 for Brazil and JIS 4502-1-2002 for Japan.

From the acquired analysis data, it is possible to estimate the positions of the transverse or longitudinal imperfections and defects within the solid material forming the shaft and thus determine whether or not this shaft meets an international standard (production or routine maintenance).

It was recently proposed to replace some solid axle shafts with tubular axle shafts, the wall of which has variable external and internal radius profiles. These new tubular shafts are particularly advantageous because they achieve a significant reduction in weight, typically of the order of 30%, and therefore allow an increase in the load transported accompanied by a reduction in the energy consumption and hence pollution. However, testing this type of tubular shaft poses a number of problems.

Indeed, due to the existence of a variable internal radius profile, it is difficult to differentiate the echoes resulting from angular zones (or corners) from those resulting from imperfections or structural defects.

Furthermore, a significant number of these imperfections and/or defects have smaller dimensions than those encountered in a solid shaft, which makes their detection even more difficult in view of the short distances traveled by ultrasound.

Finally, the positioning on some portions of a tubular shaft of some equipment, such as in particular wheels (force-fitted) and brake discs, to form an axle, is also liable to lead to additional imperfections and/or structural defects, or even increase the dimensions of some structural defects and/or imperfections caused by previous operations of hot forging and machining. As a result it is even more necessary to test these portions and the adjacent zones both during the first assembly and during maintenance operations (with or without removing the equipment from the axle). These analyses are difficult or even impossible to perform with existing test methods in some portions of the shaft when the latter is loaded with equipment.

The object of the invention is therefore to propose a non-destructive test method and apparatus to test precisely, in a manner at least semi-automatic, the majority and if possible the entirety of a tubular axle shaft (or more generally a hollow (tubular) rotational product), including when the latter is fitted with equipment.

To this end, it proposes a method for testing tubular axle shafts comprising the following steps:

a) placing on a test bench a tubular axle shaft comprising a wall with variable known external and internal radius profiles, b) placing at least one ultrasonic probe on the external or internal surface of this wall in a first site selected as a function of its profiles and the possible loading of the shaft, then analysing with each probe a first selected portion of the wall in a first selected angular sector oriented in a first longitudinal or transverse direction, in order to acquire analysis data for various relative angular positions of the shaft in relation to a probe, c) relocating at least one probe in a second site which is also selected as a function of the profiles and the possible loading of the shaft, then analysing with each relocated probe a second selected portion of the wall in a second selected angular sector oriented in a second direction opposite to the first direction, in order to acquire other analysis data for various relative angular positions of the shaft in relation to a probe, and d) creating maps from the acquired analysis data representing the transverse or longitudinal orientations and the positions of indications of echoes within the wall.

Here "indication of echo" means information obtained in a wall by reflection on an interface (material/air) or on an imperfection or on a (structural) defect. Furthermore, here "imperfection" means a part of a wall which induced an echo, the amplitude of which is lower than a selected threshold and therefore is not of a nature to result in the rejection of the shaft. Finally, here "defect" means a part of a wall which induced an echo, the amplitude of which is higher than the selected threshold and therefore is of a nature to result in rejection of the shaft.

According to the invention, the method can be divided into several variants, of which at least some characteristics can be combined with each other, and in particular:

steps b) to d), for example can be performed a first time by placing each ultrasonic probe on the external surface of the wall in order to create maps representing the positions and orientations of the indications of echoes within the wall, then at least steps b) and d) can be performed a second time by placing at least one ultrasonic probe on the internal surface of the wall in a third site which is selected as a function of its profiles, then by analysing with each probe a third selected portion of the wall in a third selected angular sector oriented in at least one selected longitudinal or transverse direction, in order to acquire analysis data for various relative angular positions of the shaft in relation to a probe, and to create maps representing the positions and orientations of the indications of echoes within the wall;

steps b) to d), for example, can be performed at least once by placing each ultrasonic probe on the external or internal surface of the wall in order to carry out an ultrasonic analysis in an angular sector oriented in a longitudinal direction, and thus create maps representing the transverse orientations and the positions of the indications of echoes within the wall, then steps b) to d) can be performed again at least once by placing at least one ultrasonic probe on the external or internal surface of the wall in order to carry out an ultrasonic analysis in an angular sector oriented in a transverse direction and thus create maps representing the longitudinal orientations and the positions of the indications of echoes within the wall;

after performing a step d), a step e) can be provided for example, in which an analysis of at least the external surface of the wall is carried out using another analysis technique which differs from that based on ultrasound, in order to acquire analysis data for various relative angular positions of at least one probe in relation to the shaft, and where applicable a step f) in which maps representing the positions and orientations of the surface indications of the wall are created from these acquired analysis data;

for example, this other analysis technique can be selected from the so-called flux leakage technique and the so-called eddy current technique;

each of the first, second and where applicable third portions of the wall can for example be analysed by means of relative longitudinal displacement of at least one probe in relation to the shaft and/or by means of electronic scanning with at least one probe;

during at least one of the steps b), c) and e) for example the various relative angular positions of the shaft in relation to each probe can be obtained either by driving this shaft in rotation in relation to each probe, or by driving each probe in rotation in relation to this shaft;

it may comprise a step g) in which the map data obtained during a step d) are compared with first reference map data previously obtained on a first reference shaft of the same type as that tested but free from defects, in order to select only the data which are representative of indications of echoes not shown on the first reference maps, and thus create "corrected" maps;

it may comprise a step h) in which the map data obtained during a step d) or g) are compared with second reference map data obtained on a second reference shaft of the same type as that tested but comprising known defects, in order to select only the data which are representative of indications of echoes representative of known defects shown on the second reference maps and thus create defect maps;

it may comprise a step i) in which the amplitudes of the map data obtained during a step d) or g) are compared with a selected threshold amplitude, in order to select only the data representative of indications of echoes with amplitudes higher than the threshold amplitude, which consequently indicate defects, and thus create defect maps;

in the event of detection of an amplitude higher than the threshold amplitude, an alarm may where applicable be generated;

it may comprise a step j) comprising displaying at least one map on a screen;

probes may be used for example which are capable of emitting ultrasound in a single variable angle direction; for example, the angle may vary between approximately 0° and approximately 70° in relation to the longitudinal or transverse direction;

as a variant for example, so-called phased array type probes can be used, capable of emitting ultrasound in directions which lie in a selected angular sector;

for example, the angular sector can be between approximately 0° and approximately 70° in relation to the longitudinal or transverse direction.

Note that steps a) to d) must be completed in this order, but that the other steps e) to j) are not necessarily completed in this order. In particular, a step j) can quite easily occur after a step d).

The invention also concerns an apparatus for testing axle shafts, which is intended to implement the method described above. This apparatus comprises more specifically:

a test bench designed to receive a tubular axle shaft with a wall which exhibits variable known external and internal radius profiles, at least one ultrasonic probe designed to analyse at least one selected portion of this wall in a selected angular sector and thus acquire analysis data, control means designed to control the test bench in order to place each probe on the external or internal surface of the wall in a first site which is selected as a function of its profiles and a possible loading of the shaft such that it analyses at least one first and at least one second selected portion of the wall respectively in at least one first and at least one second selected angular sector oriented in first and second opposing longitudinal or transverse directions, and such that it thus acquires analysis data for various relative angular positions of the shaft in relation to said probe, processing means designed to create maps from the acquired analysis data representing the longitudinal or transverse orientations and the longitudinal or transverse positions of indications of echoes within the wall.

According to the invention, this apparatus can be divided into several variants, of which at least some characteristics can be combined with each other, and in particular:

its control means can be designed to control, a first time, the relative displacement of each probe in relation to the external surface of the wall such that it acquires analysis data for various relative angular positions of the shaft in relation to said probe, then to control, a second time, the relative displacement of at least one probe in relation to the internal surface of the wall such that it analyses at least one third selected portion of the wall in at least one third selected angular sector oriented in a selected longitudinal or transverse direction, and thus acquires other analysis data for various relative angular positions of the shaft in relation to said probe. In this case, the processing means are designed to create from the acquired analysis data maps representing the positions and orientations of indications of echoes within the wall;

its control means may be designed i) to control, at least a first time, the relative displacement of each probe in relation to the external or internal surface of the wall such that it carries out an ultrasonic analysis in an angular sector oriented in a longitudinal direction and such that it acquires analysis data from which the processing means will create maps representing the transverse orientations and the positions of the indications of echoes, then ii) to control, at least a second time, the relative displacement of each probe in relation to the external or internal surface of the wall such that it carries out an ultrasonic analysis in an angular sector oriented in a transverse direction and acquires analysis data from which the processing means will create maps representing the longitudinal orientations and the positions of the indications of echoes;

it may comprise surface analysis means designed to analyse at least the external surface of the wall using another analysis technique different from that based on ultrasound, in order to acquire analysis data for various relative angular positions of the shaft in relation to a probe. In this case, the processing means may where applicable be designed to create from these analysis data (acquired through surface analysis means) maps representing the positions and orientations of the surface indications of the wall;

for example, the surface analysis means are selected from the flux leakage analysis means and the eddy current analysis means;

it may comprise displacement means designed to displace relatively in the longitudinal direction at least one probe in relation to the shaft. In this case, its control means are designed to control the displacement means so that they displace longitudinally and relatively at least one probe in relation to the shaft so that it analyses at least part of the first, second and possibly third portions of the wall; alternatively or additionally, its control means can be designed to carry out an electronic scan with at least one probe so that it analyses at least part of the first, second and possibly third portions of the wall;

its bench may be designed to drive the shaft in rotation in relation to each probe in order to define the various relative angular positions of this shaft in relation to the probe. Alternatively, the bench may be designed to drive at least one probe in rotation in relation to the shaft in order to define the various relative angular positions of this shaft in relation to said probe;

its processing means may be designed to compare the map data obtained on the shaft to be tested with the first reference map data obtained on a first reference shaft of the same type as that tested but free from defects, and to select only the data which are representative of indications of echoes not shown on the first reference maps and thus create corrected maps;

its processing means may be designed to compare the map data obtained on the shaft to be tested with the second reference map data obtained on a second reference shaft of the same type as that tested but comprising known defects, and to select only the data which are representative of indications of echoes representative of known defects shown on the second reference maps and thus create defect maps;

its processing means may be designed to compare the amplitudes of the map data obtained on the shaft to be tested with a selected threshold amplitude, and to select only the data which are representative of indications of echoes with amplitudes higher than this threshold amplitude which signal defects, and thus create defect maps;

its processing means may be designed to generate an alarm in the event of detection of an amplitude higher than the threshold amplitude;

it may comprise a screen suitable for displaying at least some of the maps that were created by its processing means;

each probe for example may be designed to emit ultrasound in a single variable angle direction, for example between approximately 0° and approximately 70° in relation to the longitudinal or transverse direction;

alternatively, each probe for example may be of the so-called phased array type and be designed to emit ultrasound in directions lying in a selected angular sector, for example between approximately 0° and approximately 70° in relation to the longitudinal or transverse direction.

Figure 2:
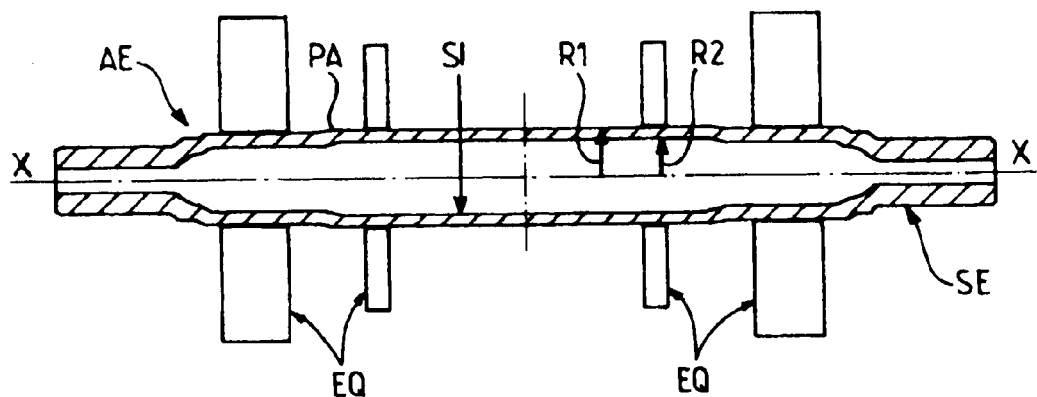
Figure 3:
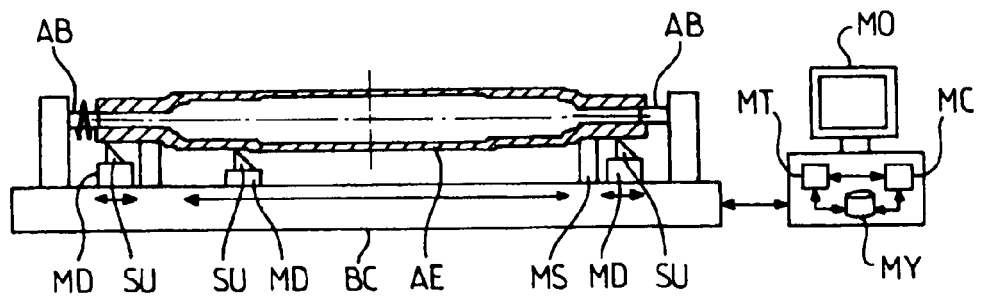
Figure 4A:
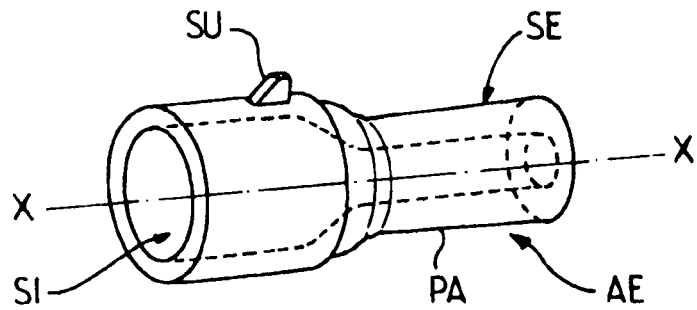
Figure 4B:
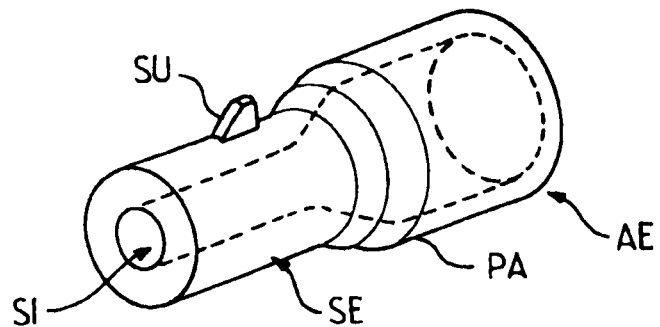
Figure 5:
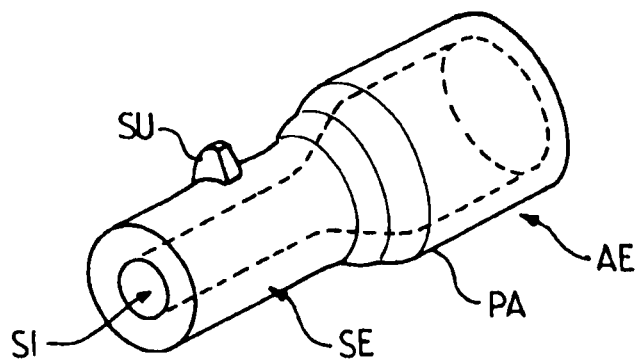
Figure 6:
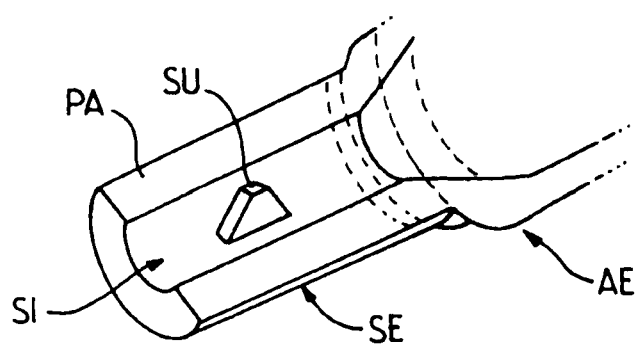
Figure 7A:
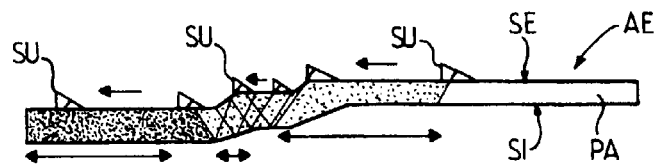
Figure 7B:
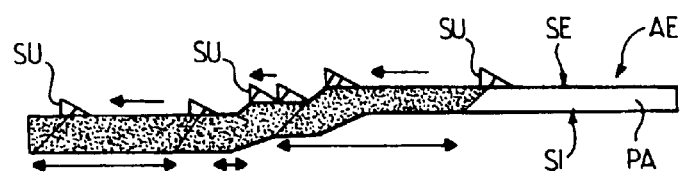
Figure 7C:
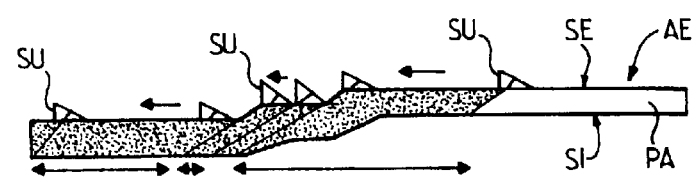
Figure 8A:
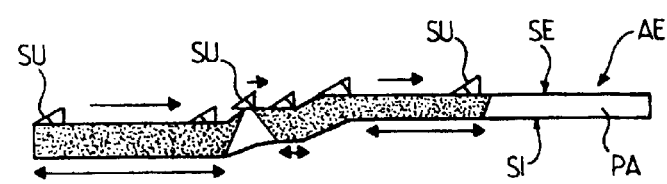
Figure 8B:
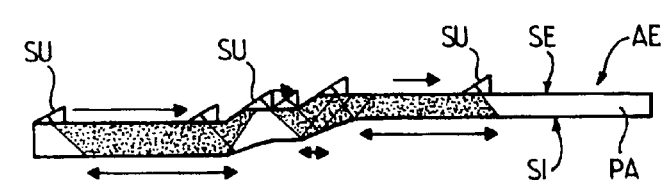
Figure 8C:
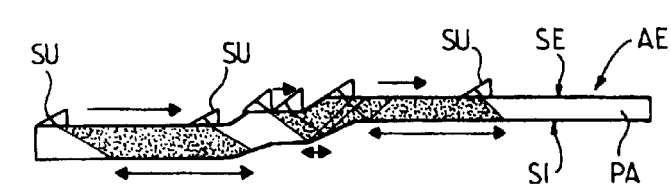
Figure 9A:
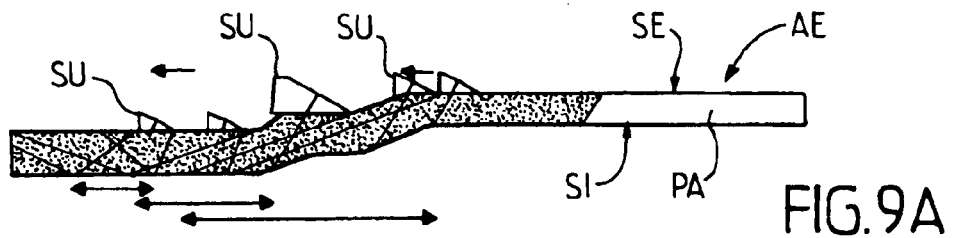
Figure 9B:
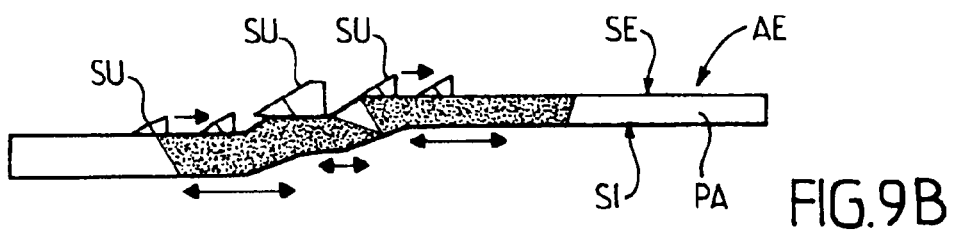
Figure 10:
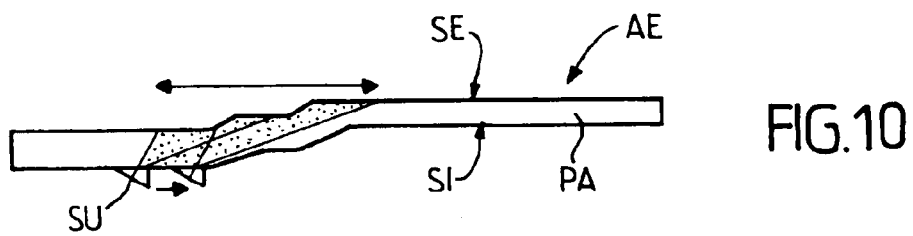
Figure 11A:
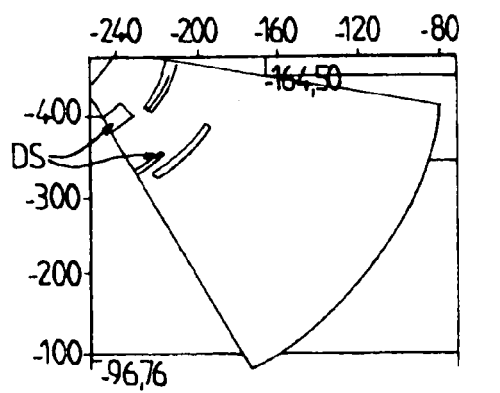
Figure 11B:
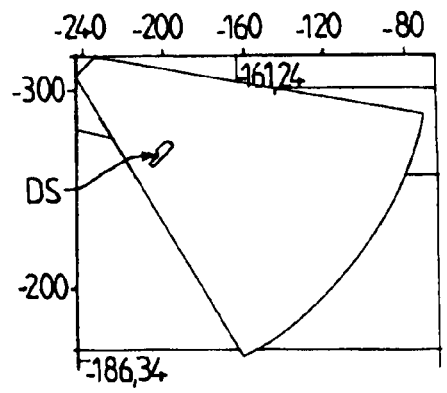

Other characteristics and advantages of the invention will become clear from the following detailed description and the attached drawings in which:

FIG. 1 shows schematically in longitudinal section an example tubular axle shaft not fitted with equipment, FIG. 2 shows schematically in longitudinal section a part of an example of a tubular axle shaft fitted with equipment, FIG. 3 shows schematically and functionally an example embodiment of a testing apparatus according to the invention, FIGS. 4A and 4B show schematically two examples of probe placement on two different selected sites of the external surface of a part of a shaft wall (in a perspective view), for a longitudinal analysis, FIG. 5 shows schematically an example of probe placement on a selected site of the external surface of a part of a shaft wall (in a perspective view), for a transverse analysis, FIG. 6 shows schematically an example of probe placement on a selected site of the internal surface of a part of a shaft wall (in a perspective view), for a longitudinal analysis, FIGS. 7A to 7C represent first portions of a part of a wall covered by three unidirectional probes displaced longitudinally from right to left for emission angles respectively equal to 30°, 45° and 60° oriented in a first longitudinal direction, FIGS. 8A to 8C depict second portions of the part of wall from FIGS. 7A to 7C covered by the same three unidirectional probes displaced longitudinally from left to right for emission angles respectively equal to 30°, 45° and 60° oriented in a second longitudinal direction, FIGS. 9A and 9B show the first and second portions of the part of wall from FIGS. 7A to 7C covered by three phased array probes for angular sectors between 30° and 70° and respectively oriented in the first and second longitudinal directions, FIG. 10 shows a third portion of a part of a wall covered by a phased array probe placed on the internal surface, for an angular sector between 30° and 70° oriented in a longitudinal direction, and FIGS. 11A and 11B show two examples of maps obtained on a same axle shaft wall.

The attached drawings can be used not only to supplement the invention, but also to contribute to its definition where applicable.

The aim of the invention is to allow the non-destructive and at least semi-automatic testing of the majority, and if possible the entirety, of a tubular axle shaft, including when the latter is fitted with equipment.

It is assumed below that the tubular shafts to be tested are intended to form part of axles on wagons for the transport of goods or passengers. However, the invention is not limited to this application. Indeed, it concerns any type of hollow (tubular) rotational product subject to in-service stresses, such as fatigue strains for example, and the wall of which has variable known external and internal radius profiles.

As shown in FIG. 1, a tubular (axle) shaft AE has a wall PA which is defined by hot forging and machining operations and which finally exhibits variable external R1 and internal R2 radius profiles. Note that the radial thickness (i.e. in a direction perpendicular to the longitudinal axis XX) is not necessarily constant. In other words, the external R1 and internal R2 radius profiles cannot necessarily be superposed homothetically.

The automatic testing of a shaft of this type, either without equipment as in the example in FIG. 1 or with equipment EQ (such as, in particular, wheels and/or brake discs) as in the example in FIG. 2, is conducted using a test apparatus of the type depicted schematically and functionally in FIG. 3.

Such an apparatus has at least one test bench BC, at least one ultrasonic probe SU (three are shown here), a control module MC and a processing module MT, and preferably a screen EC. Note that the control module MC, the processing module MT and the screen EC can form part of a microcomputer (or a workstation) MO connected to the test bench BC and to each probe SU, as shown as a non-limiting example in FIG. 3. In the following, it is assumed that the apparatus has at least two probes SU.

The test bench BC comprises supports MS for example on which can be placed an axle shaft AE (with or without equipment) and drive shafts AB designed to drive the latter in rotation according to selected angular portions, in the event of receipt of instructions generated by the control module MC.

Note that a selected angular portion may be equal to 360°, which corresponds to a full rotation. Also note that the supports MS can be omitted when the drive shafts AB can also support the axle shaft AE. Naturally any other means allowing the shaft AE to be driven in rotation may be considered. It is important to note that the important fact is that the bench BC may be charged either with driving the shaft AE in rotation in relation to the probes SU in order to define various relative angular positions of this shaft AE in relation to the probes SU, or with driving the probes SU in rotation in relation to the shaft AE in order to define various relative angular positions of this shaft AE in relation to the probes SU. In other words, the bench BC controls the relative positioning of the shaft AE in relation to the probes SU. In the following, as a non-limiting example, it is accepted that the bench BC can drive the shaft AE in rotation in relation to the probes SU.

The ultrasonic probes SU can either be arranged so as to emit ultrasound in a single direction, the angle of which is selected but can vary according to requirements, or be of the so-called phased array type, i.e. arranged so as to emit ultrasound in several directions lying in an angular sector selected according to requirements (by means of angular electronic scanning). The equivalent of a longitudinal displacement of the sensor can also be obtained using electronic scanning.

In the first case (unidirectional), each probe SU has a single sensing element designed to receive the echoes coming from the wall PA being analysed. In the second case (phased array probe), each probe SU has several sensing elements designed to receive the echoes coming from the wall PA being analysed after refraction and/or reflection (possibly multiple) at various angles. It is recalled that the sensing elements are generally made of a composite material and placed on transducers. When the sensing elements of a probe are excited, they produce a divergent analysing beam. The form of the latter and hence its general direction of incidence can be modified electronically by introducing time delays at the level of selected moments of excitation of a probe's sensing elements. The combination of a probe's sensing elements and any associated time delays which are used to produce an analysing beam in a given general direction is usually referred to as a "virtual probe". A phased array probe can thus form several (for example, several dozen) virtual probes as a function of the combinations in which it features. The excitation frequency of the transducers is typically of the order of a few Megahertz (2 to 5 MHz). When they are not excited in emission, these same sensing elements are used to detect echoes coming from the material/air or material/liquid interfaces, imperfections and defects. They form thus emitter/receiver-type sensors.

The internal R2 and external R1 radius profiles of the wall PA and the possible loading of the shaft AE are analysed, for example using CIVA 8.0 type simulation software (developed and marketed by the French Atomic Energy Commission (CEA)), so as to determine the number of probes SU which will be required to analyse the entirety or merely a selected part of the shaft AE, depending on their type (unidirectional or phased array (and in this second case, their number of sensing elements)) and the fact that they can be oriented so as to perform longitudinal or transverse analyses according to the first and second opposing directions.

Here "longitudinal analysis" means an analysis performed to search for defects and/or imperfections preferably oriented longitudinally or at a small acute angle in relation to the longitudinal direction XX (acute angle typically less than ±25°, and preferably less than ±5°). The term "obliquity" is sometimes used to refer to this defect orientation. This analysis is carried out using a beam emitted in a direction perpendicular to the longitudinal direction XX, i.e. the general direction of which is substantially contained in a plane perpendicular to the longitudinal direction XX or which makes a small acute angle (typically less than ±10°) with this perpendicular direction.

Furthermore, here "transverse analysis" means an analysis carried out to search for defects and/or imperfections preferably oriented transversally or with a small acute angle in relation to a plane perpendicular to the longitudinal direction XX (acute angle typically less than ±25°, and preferably less than ±5°). The term "obliquity" is sometimes used to refer to this defect orientation. This analysis is carried out using a beam emitted in a direction parallel to the longitudinal direction XX, i.e. the general direction of which is substantially contained in a plane which itself contains the longitudinal direction XX or which makes a small acute angle (typically less than ±10°) with this longitudinal direction.

In view of the forms of the internal R2 and external R1 radius profiles normally found in the wall PA of the shafts AE and the usual loading of the latter, the angle of emission of a unidirectional probe SU must generally be able to vary between approximately 0° and approximately 70° in relation to the longitudinal direction XX, and the angular sector of emission of a phased array probe SU must generally be between approximately 0° and approximately 70° in relation to the longitudinal direction XX.

Having determined for each probe SU the (first) selected site where it will initially have to be placed relative to the shaft AE so as to analyse a first selected portion of the wall PA in a first selected angular sector oriented in a first longitudinal or transverse direction, and the possible (second) selected site where it will have to be placed subsequently relative to the shaft AE so as to analyse a second selected portion of the wall PA in a second selected angular sector oriented in a second longitudinal or transverse direction opposite to the first direction, the probes SU can be placed in their first respective selected sites.

This relative placement of the probes SU in relation to the shaft AE can be carried out in the first selected sites which are located either on the external surface SE of the wall PA, or on the internal surface SI of this wall PA, according to requirements (and the configuration of the shaft AE). To begin with, for example, ultrasonic analyses can be performed by placing the probes SU on the external surface SE of the wall PA, then where applicable these analyses can be supplemented by subsequently placing the probes SU on the internal surface SI of the wall PA (i.e. inside the tubular shaft AE). However the reverse is also possible.

The connection between the probes SU and the internal SI or external SE surface of a wall PA can be achieved by any means known to the person skilled in the art, and in particular using glycerine or by immersion in water, preferably mixed with an anticorrosion agent.

FIGS. 4A and 4B show two examples of relative placement of a probe SU in two selected sites of the external surface SE of a part of a wall PA of a shaft AE, for a longitudinal analysis. FIG. 5 also shows an example of relative placement of a probe SU in a selected site of the external surface SE of a part of a wall PA of a shaft AE, for a transverse analysis. FIG. 6 also shows an example of relative placement of a probe SU in a selected site of the internal surface SI of a part of a wall PA of a shaft AE, for a longitudinal analysis.

It is important to note that a probe SU can analyse a portion that has been assigned to it either by remaining at the level of a selected site, or by being displaced relatively and longitudinally and/or transversally between a starting position (corresponding to the site selected initially) and an end position (corresponding to another selected site), where applicable via one or more intermediate positions (each corresponding to another selected site).

These relative displacements of probe(s) SU can be carried out using displacement means MD connected thereto. Each displacement means MD for example is a probe carrier mounted in translation in relation to the bench BC so as to be able to be displaced longitudinally in accordance with instructions generated by the control module MC. Note that each probe carrier MD may where applicable be driven in rotation so as to change the orientation of its probe SU either by 180° so that it can progress from a longitudinal or transverse analysis (general direction of emission perpendicular to the longitudinal direction XX) in a first selected angular sector oriented in a first longitudinal or transverse direction, to a longitudinal or transverse analysis in a second selected angular sector oriented in a second longitudinal or transverse direction opposite to the first direction, or by 90° so that it can progress from a longitudinal analysis in the first and second selected angular sectors to a transverse analysis in a third selected angular sector, and conversely. An analysis resulting from a combined longitudinal and transverse displacement can also be considered.

Note that the probes SU may be fixed while the bench BC can move the shaft AE longitudinally and/or drive it in rotation. It is also possible to move the probes SU longitudinally in relation to the shaft AE and to drive the latter in rotation, or conversely.

In one variant, the control module MC can be charged with carrying out an electronic scan with at least some of the probes SU so that they analyse at least a part of the first, second and possibly third portions of a wall PA. It should be noted that an electronic scan is obtained for a probe SU by using some of these sensing elements located at selected sites of its phased array and by assigning selected delays to these selected sensing elements so that they emit sequentially. This "electronic" method of displacement is advantageous because it avoids having to move a probe SU mechanically.

Note that it is also possible to combine both a longitudinal (mechanical) displacement and an electronic scan in order to allow at least some probes SU to analyse a portion of wall allocated to them. In this case, it is the control module MC which may be charged with generating the necessary instructions to the displacement means MD to move the selected probes SU relatively and longitudinally, and the necessary instructions to the selected probes SU to induce an electronic scan.

Also note that the solution used to analyse an entire portion of selected wall PA depends on the type of probe SU available and moreover, in the case of phased array probes, on the number of sensing elements constituting them. It is in fact understood that if the number of sensing elements of a probe SU is adapted to cover its assigned portion of wall PA, there is no need to provide for a mechanical longitudinal displacement because this can be substituted by an electronic scan. For example, if a probe SU has to cover a portion of wall PA with a longitudinal extension equal to 100 mm, it must comprise at least 200 sensing elements measuring 0.5 mm, for example separated in pairs by a distance equal to approximately 0.1 mm. It should be noted that the smaller the dimensions of the sensing elements, the larger the angular sectors of analysis can be. A compromise can be found between the number of sensing elements of the probes SU and the possibilities of extending the coverage offered by the electronic scanning so as to avoid mechanical longitudinal displacements.

It is also noted that the use of phased array probes is more advantageous than the use of unidirectional probes because a better continuity can be obtained on the same angular sector analysis while avoiding any angular displacement of the ultrasound source.

According to the invention, once the probes SU have been placed on the external SE or internal SI surface of a wall PA in the first sites (selected as a function of its profiles and the possible loading of the shaft AE), each of its probes SU proceeds with the analysis of the first allocated portion of the wall PA, in a first selected angular sector which is oriented in a first longitudinal or transverse direction. Each probe SU can thus acquire analysis data for the current relative angular position of the shaft AE in relation to said probe SU. By driving the shaft AE in rotation on successive selected angular sectors (here using the test bench BC, and for example with its drive shafts AB), each probe SU can carry out a new acquisition of analysis data after each angular displacement. Analysis data can thus be obtained relating to the whole circumference of each first portion of inspected wall PA.

For example, these analysis data comprise emission angles, moments of emission and reception of ultrasound (or, which is equivalent, the time intervals between the moments of emission and reception), and reception angles. They are transmitted, for example, by the probes SU to the control module MC which is charged with storing them in a memory MY corresponding to the longitudinal and angular positions of the first inspected portions in relation to a selected frame of reference, and where applicable the identifier of the probe SU used to obtain them.

Subsequently, at least some of the probes SU are relocated (relatively) on the external SE or internal SI surface of the wall PA in second sites (selected as a function of its profiles and the possible loading of the shaft AE) so that they proceed with the analysis of second portions of the wall PA that have been respectively assigned to them, in second selected angular sectors which are oriented in a second longitudinal or transverse direction opposite to the first direction.

For example, if the first direction corresponds to a direction running from left to right of the longitudinal axis XX, then the second direction corresponds to a direction running from right to left of said longitudinal axis XX. Similarly, if the first direction corresponds to a direction running from left to right of a second axis perpendicular to the longitudinal axis XX, then the second direction corresponds to a direction running from right to left of said second axis.

Each relocated probe SU can thus acquire analysis data for the current angular position of the shaft AE. By driving the shaft AE in rotation on selected angular sectors, each probe SU can carry out a new acquisition of analysis data after each angular displacement. Analysis data is thus available relating to the whole circumference of each second portion of inspected wall PA. These analysis data are transmitted, for example, by the probes SU to the control module MC which is charged with storing them in a memory corresponding to the longitudinal and angular positions of the second inspected portions in relation to a selected frame of reference, and where applicable the identifier of the probe SU used to obtain them.

As a result of this double analysis in opposing directions, all or part of an axle shaft AE can be inspected (according to requirements), as shown in FIGS. 7 to 10. More specifically:

FIGS. 7A to 7C represent the first portions of a part of a wall which can be covered by three unidirectional probes placed on the external surface SE and displaced relatively and longitudinally from right to left, for emission angles respectively equal to 30°, 45° and 60° oriented in a first longitudinal direction (running from right to left), FIGS. 8A to 8C represent the second portions of the same part of wall which can be covered by the same three unidirectional probes placed on the external surface SE and displaced relatively and longitudinally from left to right, for emission angles respectively equal to 30°, 45° and 60° oriented in a second longitudinal direction (running from left to right), FIG. 9A represents the first portions of the same part of wall which can be covered by three phased array probes placed on the external surface SE, for an angular sector between 30° and 70° oriented in a first longitudinal direction (running from right to left), FIG. 9B represents the second portions of the same part of wall which can be covered by the same three phased array probes placed on the external surface SE, for an angular sector between 30° and 70° oriented in a second longitudinal direction (running from left to right), and FIG. 10 represents the third portions of the same part of wall which can be covered by one phased array probe placed on the internal surface SI, for an angular sector between 30° and 70° oriented in a longitudinal direction (running from left to right).

Given the forms of the internal R2 and external R1 radius profiles normally found in the wall PA of shafts AE and the usual loading of the latter, the angle of emission of a unidirectional probe SU must generally be able to vary between approximately 0° and approximately 70° in relation to the longitudinal XX or transverse direction, and the angular sector of emission of a phased array probe SU must generally be between approximately 0° and approximately 70° in relation to the longitudinal XX or transverse direction.

In the examples in FIGS. 7 to 10, each bidirectional arrow represents the longitudinal extension of the (first) portion analysed by a probe SU (placed above). It is understood that the loading of an axle shaft AE notably reduces, in some parts, the longitudinal extensions of the portions which can be technically analysed (covered) by the same probe SU. This is particularly true for the parts which are located under the wheels, which have a greater probability of having structural defects caused by force fitting and/or by the loads supported, and must therefore undergo the most meticulous and complete inspection (analysis) possible.

The stored analysis data are extracted by the processing module MT, which is then charged with grouping them together as a function of the shaft zones to which they relate so as to create maps which represent the transverse or longitudinal orientations and the positions of indications of echoes within the wall PA.

It should be noted that the indications of echoes result from a reflection either on a material/air or material/liquid interface, or on an imperfection, or on a defect.

It should also be noted that the longitudinal analyses are more particularly suited to the detection of transverse imperfections and defects (which are usually the most frequent), while the transverse analyses are more particularly suited to the detection of longitudinal imperfections and defects.

Inspecting the materials in two opposite directions and therefore in very different directions of analysis enables imperfections and defects of smaller dimensions to be detected, and hence a larger number of imperfections and defects than with previous methods and test apparatus of the prior art adapted to solid shafts. But this also allows for a proper detection of oblique and inclined (or "tilted") imperfections and defects inside the wall PA.

Note that the control module MT may where applicable be arranged so as to perform "correlations" between analysis data relating to identical zones constituting the areas of coverage of first and/or second portions of wall. They can thus create "raw" maps of these areas of coverage, where applicable of a three-dimensional type (3D).

The data files constituting the raw maps are preferably stored in a memory MY. These maps can then be either displayed individually (one after the other) or in a group (several at the same time) on the screen EC to be analysed by a technician, or analysed automatically first, then converted into "corrected" maps or "defect" maps which can be displayed on the screen EC individually or in a group.

Several types of comparative analyses can be carried out on the "raw" maps.

For example, the processing module MT can be charged with comparing the data of at least some of the maps obtained on a shaft AE to be tested with first reference map data which were obtained on a first reference shaft of the same type as that tested, but free from defects. In this case, the processing module MT selects only the data which are representative of indications of echoes not shown on the first reference maps, in order to create corrected maps which it stores in the memory MY.

Alternatively or additionally, the processing module MT can be charged with comparing the data of at least some of the maps (raw or corrected) obtained on a shaft AE with data from second reference maps which were obtained on a second reference shaft of the same type as that tested, but comprising known defects. In this case, the processing module MT selects only the data which are representative of indications of echoes representative of known defects shown on the second reference maps, in order to create defect maps that it stores in the memory MY.

Alternatively or additionally, the processing module MT can be charged with comparing the amplitudes of the indications of echoes represented on at least some maps with a selected threshold amplitude. In this case, the processing module MT selects only the data which are representative of indications of echoes with amplitudes higher than the selected threshold amplitude, which consequently are assumed to result from defects, in order to create defect maps.

Furthermore, it is also possible that the processing module MT generates an alarm (audible and/or visual (displayed on the screen EC)) each time it detects an amplitude higher than the selected threshold amplitude.

Two examples of raw maps obtained on the same wall PA of an axle shaft AE are shown in FIGS. 11A and 11B. The structural defects detected are referenced DS.

As previously shown, a wall PA can be analysed by placing probes SU on its external surface SE or on its internal surface SI. However, a double analysis can also be performed, for example starting with placing the probes SU on its external surface SE then placing some of the probes SU on its internal surface SI. More precisely, in this case the probes SU are placed on the external surface SE of the wall PA in first selected sites and with these probes SU the first selected portions of the wall PA in the first selected angular sectors oriented in a first longitudinal (or transverse) direction are analysed, in order to acquire analysis data for various relative angular positions of the shaft AE in relation to the probes SU. Then, at least some of the probes SU are relocated on the external surface SE of the wall PA in second selected sites and with these probes SU the second selected portions of the wall PA in the second selected angular sectors oriented in a second longitudinal (or transverse) direction are analysed, opposite to the first, in order to acquire analysis data for various relative angular positions of the shaft AE in relation to the probes SU. Finally, at least some of the probes SU are placed on the internal surface SI of the wall PA in third selected sites and with these probes SU the third selected portions of the wall PA in the third selected angular sectors oriented in at least one longitudinal (or transverse) direction are analysed, or even two opposite directions, in order to acquire analysis data for various relative angular positions of the shaft AE in relation to the probes SU.

The processing module MT then creates, from all of the analysis data, maps representing the positions and orientations of the indications of echoes within the wall PA.

This double external and internal analysis can cover all of the portions of a wall PA to be inspected, while this may prove impossible by means of purely external analysis because of the profiles of this wall PA and/or the loading of the shaft AE.

It is also possible to carry out a first longitudinal analysis in both directions (as indicated above) externally (or internally), then a second transverse analysis in at least one direction externally (or internally), so as to create maps representing the transverse orientations and positions of the indications of echoes within the wall PA and maps representing the longitudinal orientations and positions of the indications of echoes within the same wall PA.

It is also possible to carry out a first longitudinal analysis in both directions externally, then a second transverse analysis in at least one direction internally.

It is also possible to carry out a first transverse analysis in both directions internally, then a second analysis in at least one direction externally.

As a general rule, all the combinations of longitudinal and transverse analyses internally and externally can be considered.

Note that, in some cases, the internal analyses may require reboring of at least the ends of the tubular axle shaft AE so as to allow at least one probe SU to be placed inside this shaft AE against the internal surface SI of its wall PA, and where applicable its relative displacement by suitable displacement means MD.

Also note that the sites for placement of the probes SU, the various angles or various angular sectors of analysis by ultrasound of each of the probes SU and the portions of wall assigned to the various probes, can where applicable be selected as a function of stress(es). Thus, it can be considered that a part of a test be conducted with a beam, the general direction of which is substantially contained in a plane which itself contains the longitudinal direction XX and on the portions of wall exhibiting in pairs selected rates of coverage, for example 50%, and/or that a part of a test be conducted with successive beams, the general directions of which are substantially contained in planes which form acute angles with this longitudinal direction XX which are between 0° and +20° and between 0° and −20°. Furthermore, the angle of inclination of the sensing elements of a probe SU can be selected in accordance with requirements. As a non-limiting example, an angle of 45° in relation to the longitudinal direction XX can be selected.

It is also noted, as the person skilled in the art is aware, that the gain of each transducer must be adjusted during a calibration phase, for example so that the amplitude of the signal obtained on the first echo coming from an interface of the wall PA corresponds to an amplitude equal for example to approximately 50% of the total amplitude dynamics used for the maps.

Furthermore, the calibration phase preferably also includes a first part dedicated to obtaining said reference maps which are representative of the results of ultrasonic analyses carried out on a reference tubular axle shaft of the same type as those to be tested, but sound (i.e. free from imperfections and structural defects). Indeed, this first part of the calibration phase enables the echoes induced by the geometries of the wall PA (and in particular the corners and more generally the areas in which the internal R2 or external R1 radius varies significantly) to be known in advance and thus differentiated from those induced by the imperfections and structural defects in the tubular axle shafts AE to be tested.

Similarly, the calibration phase can also include a second part dedicated to obtaining said reference maps which are representative of the results of ultrasonic analyses carried out on a reference tubular axle shaft of the same type as those to be tested, but which reference comprises characteristic structural or artificial defects (such as for example characteristic notches or cavities) defined in the selected sites. These characteristic structural or artificial defects are defined according to specifications and/or standards which establish a sorting threshold between imperfections and defects. When the amplitude of the signal coming from echoes on natural defects is lower than the sorting threshold, there is an imperfection. If it is higher than the threshold, there is a defect. In effect, this second part of the calibration phase enables echoes that are induced by characteristic structural or artificial defects to be known in advance and thus allows easier detection on the maps, by comparison with a sorting threshold, of "objects" which induce echoes (or signatures) of similar types in the tubular axle shafts AE to be tested.

Once the longitudinal and/or transverse ultrasonic analysis of a tubular axle shaft AE has been completed, it is then possible to carry out at least one additional analysis of another type. For example, an analysis of the external surface SE of the wall PA can be carried out in order to acquire surface analysis data for various relative positions of the shaft AE in relation to the surface analysis means.

Surface analysis techniques which can be used include in particular the so-called flux leakage technique and the so-called eddy current technique. Some of these techniques are beneficial because they provide surface analysis data from which maps representing the positions and orientations of surface defects of the wall PA can be created. The data files of these surface defect maps are preferably stored in a memory MY such that said surface defect maps can be displayed individually (one after the other) or in a group (several at the same time), where applicable with maps of structural defects (obtained by ultrasound), on the screen EC in order to be analysed by a technician and/or to be compared with maps obtained with the probes SU. This can also allow automatic comparison by the apparatus of surface defect maps and maps obtained by ultrasound.

It is noted that an MPI ("Magnetic Particle Inspection") type surface analysis can also be carried out. It should be noted that this technique involves covering the external surface SE of a wall PA using magnetic particles and a developer, then magnetising the wall to be inspected, then visually observing (with the eyes) under a UV (ultraviolet) light the irregularities of orientation of these magnetic particles, irregularities of orientation linked to the presence of defects or imperfections. The disadvantage of this surface analysis technique is the fact that it does not at present provide surface defect maps, and hence relies exclusively on the visual observation by the technician carrying out the test on shaft AE, and subsequently requires a visual and non-automatic comparison with the maps obtained by ultrasound. One is then dependent on the interpretation by the operator and its associated risks.

It is also noted that the maps referred to above may be of any type known to the person skilled in the art, and in particular of the A-Scan, B-Scan, C-Scan, D-Scan, and S-Scan (or Sector Scan) type. For purely illustrative purposes, for example C-Scan type maps can be created (which provide a representation of location of the imperfection in relation to the geometry of the part) and where applicable S-Scan type maps (which provide indications of location in the volume, with fixed probe position).

Owing to the invention, it is possible to detect imperfections and defects approximately 2 mm thick (i.e. approximately 5% of the nominal thickness of the wall PA in the radial direction), approximately 5 mm long and approximately 1 mm wide. Furthermore, longitudinal and transverse imperfections and defects exhibiting an obliquity at acute angles typically smaller than ±25° and preferably smaller than ±5° can be detected. Moreover, longitudinal or transverse cavities (or "flaws") exhibiting disorientation angles (or "tilt angles") of up to approximately 60° can be detected.

The invention is not limited to the examples of the method and apparatus for testing tubular axle shafts described above merely as examples, but it includes all the variants which may be considered by the person skilled in the art within the framework of the claims below.

The invention claimed is:

1. A method for testing axle shafts using at least one ultrasonic probe, comprising:
    a) placing on a test bench a tubular axle shaft comprising a wall exhibiting variable known external and internal radius profiles;
    b) placing at least one ultrasonic probe on an external or internal surface of the wall in a first site selected as a function of its profiles and a possible loading of the shaft, then analyzing with each probe a first selected portion of the wall in a first selected angular sector oriented in a first longitudinal or transverse direction, so as to acquire analysis data for various relative angular positions of the shaft in relation to the probe;
    c) relocating at least one probe in at least one second site selected as a function of the profiles of the wall and the possible loading of the shaft, then analyzing with each probe a second selected portion of the wall in a second selected angular sector oriented in a second direction opposite to the first direction, so as to acquire other analysis data for various relative angular positions of the shaft in relation to the probe; and
    d) creating from the acquired analysis data maps representing transverse or longitudinal orientations and positions of indications of echoes within the wall.

2. A method according to claim 1, wherein operations b) to d) are carried out a first time by placing each ultrasonic probe on the external surface of the wall so as to create maps representing the positions and orientations of the indications of echoes within the wall, then at least operations b) and d) are carried out a second time by placing at least one ultrasonic probe on the internal surface of the wall in at least one third site selected as a function of its profiles, then analyzing with each probe a third selected portion of the wall in a third selected angular sector oriented in at least one selected longitudinal or transverse direction, so as to acquire analysis data for various relative angular positions of the shaft in relation to the probe, and to create maps representing the positions and orientations of the indications of echoes within the wall.

3. A method according to claim 1, wherein operations b) to d) are carried out at least once by placing each ultrasonic probe on the external or internal surface of the wall so as to carry out an ultrasonic analysis in an angular sector oriented in a longitudinal direction, and thus create maps representing the transverse orientations and the positions of the indications of echoes within the wall, then operations b) to d) are carried out again at least once by placing at least one ultrasonic probe on the external or internal surface of the wall so as to carry out an ultrasonic analysis in an angular sector oriented in a transverse direction and thus create maps representing the longitudinal orientations and the positions of the indications of echoes within the wall.

4. A method according to claim 1, wherein after having performed the creating d), further comprising: e) carrying out an analysis of at least the external surface of the wall using another analysis technique different from that based on ultrasound, so as to acquire analysis data for various relative angular positions of the shaft in relation to a probe.

5. A method according to claim 4, wherein after the carrying out e) further comprising: f) creating maps from these acquired analysis data representing the positions and orientations of the surface indications of the wall.

6. A method according to claim 4, wherein the other analysis technique is selected from a group consisting of a flux leakage technique and an eddy current technique.

7. A method according to claim 1, wherein each of the first, second, and possibly third portions of the wall is analyzed via relative longitudinal displacement of at least one probe in relation to the shaft and/or by electronic scanning with at least one probe.

8. A method according to claim 4, wherein in at least one of operations b), c) and e), the various relative angular positions of the shaft in relation to a probe are obtained by driving the shaft in rotation in relation to a probe.

9. A method according to claim 4, wherein in at least one of operations b), c) and e), the various relative angular positions of the shaft in relation to a probe are obtained by driving at least one probe in rotation in relation to the shaft.

10. A method according to claim 1, further comprising: e) comparing the data map obtained during the creating d) with first reference data map obtained on a first reference shaft of the same type as that tested but free from defects, so as to select only the data which are representative of indications of echoes not shown on the first reference maps and thus create corrected maps.

11. A method according to claim 10, further comprising: f) comparing the data map obtained during operations d) or e) with second reference data map obtained on a second reference shaft of the same type as that tested but comprising known defects, so as to select only the data which are representative of indications of echoes representative of known defects shown on the second reference maps, and thus create defect maps.

12. A method according to claim 10, further comprising: f) comparing amplitudes of the data map obtained during operation d) or e) are with a selected threshold amplitude so as to select only the data which are representative of indications of echoes with amplitudes higher than the threshold amplitude which signal defects, and thus create defect maps.

13. A method according to claim 12, wherein in an event of detection of an amplitude higher than the threshold amplitude, an alarm is generated.

14. A method according to claim 1, further comprising: e) displaying at least one map on a screen.

15. A method according to claim 1, wherein probes are used which are capable of emitting ultrasound in a single variable angle direction.

16. A method according to claim 15, wherein the angle varies between approximately 0° and approximately 70° in relation to the longitudinal or transverse direction.

17. A method according to claim 1, wherein phased array type probes are used that are capable of emitting ultrasound in directions lying in a selected angular sector.

18. A method according to claim 17, wherein the angular sector is between approximately 0° and approximately 70° in relation to the longitudinal or transverse direction.

19. An apparatus for testing axle shafts, comprising:
   i) a test bench arranged to receive a tubular axle shaft having one wall with variable known external and internal radius profiles;
   ii) at least one ultrasonic probe arranged to analyze at least one selected portion of said wall in a selected angular sector and thus acquire analysis data;
   iii) control means arranged to control the test bench so as to place each probe on an external or internal surface of said wall in a first site selected as a function of its profiles and a possible loading of said shaft such that it analyses at least one first and at least one second selected portion of said wall respectively in at least one first and at least one second selected angular sector oriented in first and second opposing longitudinal or transverse directions, and such that it acquires thus analysis data for various relative angular positions of said shaft in relation to a probe;
   iv) processing means arranged to create from said acquired analysis data maps representing the transverse or longitudinal orientations and the positions of indications of echoes within said wall.

20. An apparatus according to claim 19, wherein said control means are arranged to control a first time the relative displacement of at least one probe in relation to the external surface of said wall such that it acquires analysis data for various relative angular positions of said shaft in relation to said probe, then to control a second time the relative displacement of at least one probe in relation to the internal surface of said wall such that it analyses at least one third selected portion of said wall in at least one third selected angular sector oriented in a selected longitudinal or transverse direction and such that it thus acquires other analysis data for various relative angular positions of said shaft in relation to said probe, and wherein said processing means are arranged to create from said acquired analysis data maps representing the positions and orientations of indications of echoes within said wall.

21. An apparatus according to claim 19, wherein said control means are arranged: i) to control at least a first time the relative displacement of at least one probe in relation to the external or internal surface of said wall such that it carries out an ultrasonic analysis in an angular sector oriented in a longitudinal direction, and such that it acquires analysis data from which said processing means will create maps representing the transverse orientations and the positions of the indications of echoes, then ii) to control at least a second time the relative displacement of at least one probe in relation to the external or internal surface of said wall such that it carries out an ultrasonic analysis in an angular sector oriented in a transverse direction, and such that it acquires analysis data from which said processing means will create maps representing the longitudinal orientations and the positions of the indications of echoes.

22. An apparatus according to claim 19, further comprising: v) surface analysis means arranged to analyze at least the external surface of said wall by another analysis technique different from that based on ultrasound, so as to acquire analysis data for various relative angular positions of said shaft in relation to a probe.

23. An apparatus according to claim 22, wherein said processing means are arranged to create from these analysis data acquired through said surface analysis means maps representing the positions and orientations of the surface indications of said wall.

24. An apparatus according to claim 22, wherein said surface analysis means are selected from a group consisting of flux leakage analysis means and eddy current analysis means.

25. An apparatus according to claim 19, further comprising: v) displacement means arranged to displace relatively in the longitudinal direction at least one probe in relation to said shaft, and said control means are arranged to control said displacement means such that they displace longitudinally and relatively at least one probe in relation to said shaft so that it analyses at least a part of said first, second, and where applicable third portions of said wall.

26. An apparatus according to claim 19, wherein said control means are arranged to perform an electronic scan with at least one probe so that it analyses at least a part of said first, second, and where applicable third portions of said wall.

27. An apparatus according to claim 19, wherein said test bench is arranged to drive said shaft in rotation in relation to each probe so as to define the various relative angular positions of said shaft in relation to each probe.

28. An apparatus according to claim 19, wherein said test bench is arranged to drive at least one probe in rotation in relation to said axle so as to define the various relative angular positions of said shaft in relation to each probe.

29. An apparatus according to claim 19, wherein said processing means are arranged to compare the data map obtained on said shaft to be tested with a first reference data map obtained on a first reference shaft of the same type as that tested but free from defects, and to select only the data which are representative of indications of echoes not shown on said first reference maps and thus create corrected maps.

30. An apparatus according to claim 19, wherein said processing means are arranged to compare the data map obtained on said shaft to be tested with a second reference map data obtained on a second reference shaft of the same type as that tested but comprising known defects, and to select only the data which are representative of indications of echoes representative of known defects shown on said second reference maps, and thus create defect maps.

31. An apparatus according to claim 19, wherein said processing means are arranged to compare the amplitudes of the data map obtained on said shaft to be tested with a selected threshold amplitude, and to select only the data which are representative of indications of echoes with amplitudes higher than said threshold amplitude which signal defects, and thus create defect maps.

32. An apparatus according to claim 31, wherein said processing means are arranged to generate an alarm in an event of detection of an amplitude higher than said threshold amplitude.

33. An apparatus according to claim 19, further comprising: v) a screen capable of displaying at least some of said maps created by said processing means.

34. An apparatus according to claim 19, wherein said probes are capable of emitting ultrasound in a single variable angle direction.

35. An apparatus according to claim 34, wherein said angle direction varies between approximately 0° and approximately 70° in relation to the longitudinal or transverse direction.

36. An apparatus according to claim 19, wherein said probes are of phased array type and are capable of emitting ultrasound in directions lying in a selected angular sector.

37. An apparatus according to claim 36, wherein said angular sector is between approximately 0° and approximately 70° in relation to the longitudinal or transverse direction.

* * * * *